United States Patent [19]
Rosenberg et al.

[11] Patent Number: 6,121,240
[45] Date of Patent: *Sep. 19, 2000

[54] UROKINASE RECEPTOR LIGANDS

[75] Inventors: Steven Rosenberg, Oakland; Kerry L. Spear, Raleigh; Eric J. Martin, El Cerrito, all of Calif.

[73] Assignee: Chiron Corporation, Emeryville, Calif.

[*] Notice: This patent is subject to a terminal disclaimer.

[21] Appl. No.: 08/765,275

[22] PCT Filed: Jun. 7, 1996

[86] PCT No.: PCT/US96/09648

§ 371 Date: Dec. 20, 1996

§ 102(e) Date: Dec. 20, 1996

[87] PCT Pub. No.: WO96/40747

PCT Pub. Date: Dec. 19, 1996

Related U.S. Application Data

[63] Continuation-in-part of application No. 08/485,021, Jun. 7, 1995, Pat. No. 5,747,458.

[51] Int. Cl.$^7$ ............................ A61K 38/06; A61K 38/07

[52] U.S. Cl. .............................. 514/18; 514/2; 530/330; 530/331; 530/332

[58] Field of Search ............................ 562/575; 514/613, 514/2, 18; 530/330, 331, 332

[56] References Cited

U.S. PATENT DOCUMENTS

| | | | |
|---|---|---|---|
| 4,708,871 | 11/1987 | Geysen | 424/88 |
| 4,833,092 | 5/1989 | Geysen | 436/501 |
| 5,194,392 | 3/1993 | Geysen | 436/518 |
| 5,536,853 | 7/1996 | Spellmeyer et al. | 549/441 |

FOREIGN PATENT DOCUMENTS

| | | |
|---|---|---|
| WO 91/19735 | 12/1991 | WIPO . |
| WO 94/06451 | 3/1994 | WIPO . |
| WO 95/27729 | 10/1995 | WIPO . |
| WO 95/29189 | 11/1995 | WIPO . |

OTHER PUBLICATIONS

Appella et al., "The Receptor–binding Sequence of Urokinase", *J Biol Chem* (Apr. 5, 1987) 262:4437–40.
Behrendt et al., "Binding of the Urokinase–type Plasminogen Activator to Its Cell Surface Receptor is Inhibited by Low Doses of Suramin", *J Biol Chem* (Mar. 15, 1993) 268:5985–89.
Carmeliet et al., "Biological Effects of Inactivation of the Genes for Tissue–type Plasminogen Activator, Urokinase–type Plasminogen Activator and Plasminogen Activator Inhibitor–1 in Mice", *Fibrinolysis* (1993) 7 Suppl. 1:27–28.
Cekuoliene et al., "Oxamido and Succinamidotetraacetic Acids and Their Derivatives", *Chemical Abstracts* (1974) 80:382, Abstract No. 145348F.
Crowley et al., "Prevention of Metastasis by Inhibition of the Urokinase Receptor", *Proc Natl Acad Sci USA* (Jun., 1993) 90:5021–25.
Foekens et al., "Prognostic Value of Urokinase–type Plasminogen Activator in 671 Primary Breast Cancer Patients", *Cancer Res* (Nov. 1, 1992) 52:6101–05.
Goodson et al., "High-affinity Urokinase Receptor Antagonists Identified With Bacteriophage Peptide Display", *Proc Natl Acad Sci USA* (1994) 91:7129–7133.
Kobayashi et al., "Saturation of Tumour Cell Surface Receptors for Urokinase–type Plasminogen Activator by Amino–terminal Fragment and Subsequent Effect on Reconstituted Basement Membranes Invasion", *Br J. Cancer* (1993) 67:537–44.
Mignatti et al., "Expression of the Urokinase Receptor in Vascular Endothelial Cells is Stimulated by Basic Fibroblast Growth Factor", *J Cell Biol* (Jun., 1991) 113:1193–202.
Min et al., "cDNA for Mo3, A Monocyte Activation Antigen, Encodes the Human Receptor for Urokinase Plasminogen Activator", *J Immunol* (Jun. 1, 1992) 148:3636–42.
Niedbala et al., "Tumor Necrosis Factor Induction of Endothelial Cell Urokinase–type Plasminogen Activator Mediated Proteolysis of Extracellular Matrix and Its Antagonism by γ–Interferon", *Blood* (Feb. 1, 1992) 79:678–87.
Nykjær et al., "An Activation Antigen in Human T Lymphocytes", *J Immunol* (1994) 152:505–16.
Odekon et al., "Urokinase–type Plasminogen Activator Mediates Basic Fibroblast Growth Factor–Induced Bovine Endothelial Cell Migration Independent of Its Proteolytic Activity", *J Cell Physiol* (1992) 150:258–63.

(List continued on next page.)

*Primary Examiner*—Prema Mertz
*Assistant Examiner*—Michael Pak
*Attorney, Agent, or Firm*—Sharon Fujita; Robert P. Blackburn

[57] ABSTRACT

Compounds of the invention inhibit urokinase plasminogen activator or uPAR:

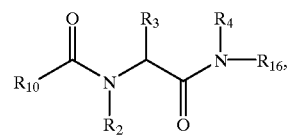

where $R_{10}$ is —$CH(R_9)XCH(R_1)(R_{11})$ or a capping group, where X is $NR_{12}$, $CR_{12}R_{15}$, O, S, $SR_{12}$, or $SR_{12}R_{15}$; $R_1$, $R_9$, $R_{11}$, $R_{12}$ $R_{15}$ are each H, lower alkyl, lower alkenyl, lower alkynyl, aryl, aralkyl, aryl-alkenyl, aryl-alkynyl, arylcycloalkyl, substituted with 0–3 halo, OH, $NH_2$, lower alkyl, halo-lower alkyl, lower alkoxy, lower alkylamino, lower alkylthio, CN or $NO_2$; $R_{16}$ is —$CH(R_5)C(=O)NH_2$, H, lower alkyl, cycloalkyl, or lower alkenyl; $R_2$ is aryl or aralkyl, unsubstituted or substituted with 1–3 halo, OH, $NH_2$, CN, $NO_2$, lower alkyl, halo-lower alkyl, lower alkoxy, lower alkylamino, lower alkylthio, or cycloalkyl; $R_3$ and $R_5$ are each independently H or lower alkyl; $R_4$ is —$CH_2C(=O)NR_{13}R_{14}$, where $R_{13}$ is H, lower alkyl, phenyl or benzyl, and $R_{14}$ is H, aryl, or aralkyl, where $R_6$ and $R_7$ are each independently H, OH, $NH_2$, CN, $NO_2$, lower alkyl, halo-lower alkyl, lower alkoxy, lower alkylamino, lower alkylthio, or cycloalkyl, and n and m are each independently an integer from 1 to 3; and pharmaceutically acceptable acid addition salts thereof.

18 Claims, No Drawings

OTHER PUBLICATIONS

Ossowski et al., "Antibodies to Plasminogen Activator Inhibit Human Tumor Metastasis", *Cell* (Dec., 1983) 35:611–19.

Ossowski, "In Vivo Invasion of Modified Chorioallantoic Membrane by Tumor Cells: the Role of Cell Surface–bound Urokinase", *J Cell Biol* (Dec. 1988) 107:2437–45.

Ploug et al., "Ligand Infection between Urokinase–Type Plasminogen Activator and Its Receptor Probed with 8–Anilino–1–naphthalenesulfonate. Evidence for a Hydrophobic Binding Site Exposed Only on the Intact Receptor", *Biochemistry* (1994) 33:8991–97.

Pyke et al., "Urokinase–type Plasminogen Activator is Expressed in Stromal Cells and Its Receptor in Cancer Cells at Invasive Foci in Human Colon Adenocarcinomas", *Am J Path* (May, 1991) 138:1059–67.

Pyke et al., "Receptor for Urokinase is Present in Tumor–associated Macrophages in Ductal Breast Carcinoma", *Cancer Res* (Apr. 15, 1993) 53:1911–15.

Rabbani et al., "Structural Requirements for the Growth Factor Activity of the Amino–terminal Domain of Urokinase", *J Biol Chem* (Jul. 15, 1992) 267:14151–56.

Schlechte et al., "Invasion of Extracellular Matrix by Colon Cancer Cells: Dependence on Urokinase Receptor Display", *Cancer Comm* (1990) 2:173–79.

Takano et al., "Suramin, an Anticancer and Angiosuppresive Agent, Inhibits Endothelial Cell Binding of Basic Fibroblast Growth Factor, Migration, Proliferation, and Indution of Urokinase–type Plasminogen Activator", *Cancer Res* (May 15, 1994) 54:2654–60.

Weinstat–Saslo et al., "Angiogenesis and Colonization in the Tumor Metastatic Process: Basic and Applied Advances", *FASEB J* (Apr., 1994) 8:401–407.

UROKINASE RECEPTOR LIGANDS

This is a 371 of PCT/US96/09648 filed Jun. 7, 1996 which is a continuation-in-part of U.S. application Ser. No. 08/485,021, filed Jun. 7, 1995, now U.S. Pat. No. 5,747,458, to which priority is claimed under 35 U.S.C. § 120.

FIELD OF THE INVENTION

This invention relates to the fields of ligands of the urokinase plasminogen activator receptor, and methods for using and preparing the same.

BACKGROUND OF THE INVENTION

Urokinase-type plasminogen activator (uPA) is a multi-domain serine protease, having a catalytic "B" chain (amino acids 144–411), and an amino-terminal fragment ("ATF", aa 1–143) consisting of a growth factor-like domain (4–43) and a kringle (aa 47–135). The uPA kringle appears to bind heparin, but not fibrin, lysine, or aminohexanoic acid. The growth factor-like domain bears some similarity to the structure of epidermal growth factor (EGF), and is thus also referred to as an "EGF-like" domain. The single chain pro-uPA is activated by plasmin or other proteases, cleaving the chain into the two chain active form, which is linked together by a disulfide bond.

uPA binds to its specific cell surface receptor (uPAR). The binding interaction is apparently mediated by the EGF-like domain (S.A. Rabbani et al., *J Biol Chem* (1992) 267:14151–56). Cleavage of pro-uPA into active uPA is accelerated when pro-uPA and plasminogen are receptor-bound. Thus, plasmin activates pro-uPA, which in turn activates more plasmin by cleaving plasminogen. This positive feedback cycle is apparently limited to the receptor-based proteolysis on the cell surface, since a large excess of protease inhibitors is found in plasma, including $\alpha_2$ antiplasmin, and PAI-1.

Plasmin can activate or degrade extracellular proteins such as fibrinogen, fibronectin, and zymogens, particularly of the matrix metalloproteinases. Plasminogen activators thus can regulate extracellular proteolysis, fibrin clot lysis, tissue remodeling, developmental cell migration, inflammation, and metastasis. Accordingly, there is great interest in developing uPA inhibitors and uPA receptor antagonists. E. Appella et al., *J Biol Chem* (1987) 262:4437–40, determined that receptor binding activity is localized in the EGF-like domain, and that residues 12–32 appear to be critical for binding. The critical domain alone ($uPA_{12-32}$) bound uPAR with an affinity of 40 nM (about 100 fold less than intact ATF).

Recent studies have shown that the invasiveness of human tumor cell lines in vitro correlates with surface bound urokinase, and that urokinase production itself is an independent prognostic indicator in human breast cancer (W. Schlechte et al., *Cancer Comm* (1990) 2:173–79; H. Kobayashi et al., *Br J Cancer* (1993) 67:537–44; J. A. Foekens et al., *Cancer Res* (1992) 52:6101–05). It has also been shown in both breast and colon cancer that urokinase is often made by stromal cells (fibroblasts and macrophages), whereas the urokinase receptor is found on tumor cells (C. Pyke et al., *Cancer Res* (1993) 53:1911–15; C. Pyke et al., *Am J Path* (1991) 138:1059–67). UPAR has independently been identified as a monocyte activation antigen, Mo3, whose expression is induced in these inflammatory cells upon activation (H.Y. Min et al., *J Immunol* (1992) 148:3636–42), as well as an activation antigen on human T lymphocytes (A. Nykjxr et al., *J Immunol* (1994) 152:505–16). Urokinase plasminogen activator "knock-out" mice (in which the uPA gene is inactivated or deleted throughout the body) have been developed, and their macrophages are deficient in extracellular matrix degradation in vitro (P. Carmeliet et al., *Fibrinolysis* (1993) 7 *Suppl.* 1:27–28). In addition, these mice show greatly reduced smooth muscle cell migration/proliferation after arterial wounding, suggesting a possible role for uPA/uPAR in post-angioplasty restenosis.

The induction of urokinase and its receptor by agents known to be angiogenic in vivo, such as bFGF, vEGF, and TNFα, suggests a role for cell surface urokinase in angiogenesis (P. Mignatti et al., *J Cell Biol* (1991) 113:1193–202; L. E. Odekon et al., *J Cell Physiol* (1992) 150:258–63; M. J. Niedbala et al., *Blood* (1992) 79:678–87). Although many factors are likely to be angiogenic in pathological conditions, degradation of extracellular matrix by capillary endothelial cells and release of matrix-bound pro-angiogenic factors by cell surface plasmin is likely a common step in these processes (D. Weinstat-Saslo et al., *FASEB J* (1994) 8:401–07). This is further supported by the observation that several known anti-angiogenic substances reduce uPA expression (S.

Takano et al., *Cancer Res* (1994) 54:2654–60). In vivo studies have shown that prevention of urokinase-receptor binding, by urokinase antibodies or competition with inactive urokinase mutants, dramatically reduces or eliminates the metastatic potential of human prostate tumor cells in nude mice (C. W. Crowley et al., *Proc Natl Acad Sci USA* (1993) 90:5021–25; L. Ossowski et al., *Cell* (1983) 35:611–19; L. Ossowski, *J Cell Biol* (1988) 107:2437–45). It has recently been shown in both in vitro and syngeneic in vivo models that the protein uPAR antagonists are anti-angiogenic (Mn et al., *Cancer Res* (1996) 56:2428).

Although a primary role of uPAR is in the focusing of uPA dependent plasminogen activation to the cell surface, it also has other functions. For instance, uPAR is involved in cell adhesion, functioning as a uPA dependent vitronectin receptor (Wei et al., *J Biol Chem* (1994) 269:32380–88). More recently, it has been shown that uPAR interacts with integrins and is likely involved in cell shape changes and cell migration (Kindzelskii et al., *J Immunol* (1996) 156:297).

To date, only two small molecules have been described which inhibit the uPA:uPAR interaction (suramin: N. Behrendt et al., *J Biol Chem* (1993) 268:5985–89; and 8-anilinonaphthalene sulfonic acid: M. Ploug et al., *Biochemistry* (1994) 33:8991–97). Unfortunately, these compounds are effective only at micromolar concentrations.

SUMMARY OF THE INVENTION

We have now invented compounds which bind tightly to uPAR and are capable of inhibiting the uPA:uPAR interaction, and thus useful for treating disorders or diseases mediated by uPA and/or uPAR. The compounds have the general structure:

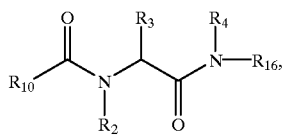

where $R_{10}$ is

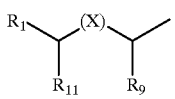

or a capping group, where X is $NR_{12}$, $CR_{12}R_{15}$, O, S, $SR_{12}$, or $SR_{12}R_{15}$; $R_1$, $R_9$, $R_{11}$, $R_{12}$ $R_{15}$ are each independently H, lower alkyl, lower alkenyl, lower alkynyl, aryl, aralkyl, aryl-alkenyl, aryl-alkynyl, aryl-cycloalkyl, unsubstituted or substituted with 1–3 halo, OH, NH2, lower alkyl, halo-lower alkyl, lower alkoxy, lower alkylamino, lower alkylthio, CN or $NO_2$; $R_{16}$ is

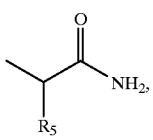

H, lower alkyl, cycloalkyl, or lower alkenyl; $R_2$ is aryl or aralkyl, unsubstituted or substituted with 1–3 halo, OH, $NH_2$, CN, $NO_2$, lower alkyl, halo-lower alkyl, lower alkoxy, lower alkylamino, lower alkylthio, or cycloalkyl; $R_3$ and $R_5$ are each independently H or lower alkyl;

$R_4$ is

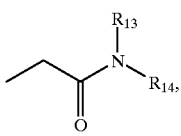

where $R_{13}$ is H, lower alkyl, phenyl or benzyl, and $R_{14}$ is H, aryl, aralkyl, or especially

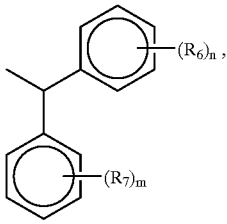

where $R_6$ and $R_7$ are each independently H, OH, $NH_2$, CN, $NO_2$, lower alkyl, halo-lower alkyl, lower alkoxy, lower alkylamino, lower alkylthio, or cycloalkyl, and n and m are each independently an integer from 1 to 3 inclusive; and pharmaceutically acceptable acid addition salts thereof.

Another aspect of the invention is the method of treating tumor angiogenesis by administering a compound of the invention to a subject in need thereof.

Another aspect of the invention is a pharmaceutical formulation comprising an effective amount of a compound of the invention and a pharmaceutically acceptable excipient.

DETAILED DESCRIPTION

Definitions

The terms "compound of the invention" and "compound of Formula 1" refer to a compound of the formula:

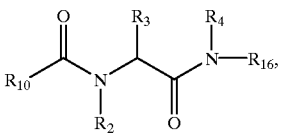

where $R_{10}$ is

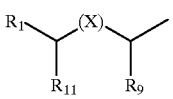

or a capping group, where X is $NR_{12}$, $CR_{12}R_{15}$, O, S, $SR_{12}$, or $SR_{12}R_{15}$; $R_1$, $R_9$, $R_{11}$, $R_{12}$ $R_{15}$ are each independently H, lower alkyl, lower alkenyl, lower alkynyl, aryl, aralkyl, aryl-alkenyl, aryl-alkynyl, aryl-cycloalkyl, substituted with 0–3 halo, OH, NH2, lower alkyl, halo-lower alkyl, lower alkoxy, lower alkylamino, lower alkylthio, CN or $NO_2$;

$R_{16}$ is

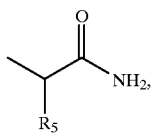

H, lower alkyl, cycloalkyl, or lower alkenyl;

$R_2$ is aryl or aralkyl, unsubstituted or substituted with 1–3 halo, OH, $NH_2$, CN, $NO_2$, lower alkyl, halo-lower alkyl, lower alkoxy, lower alkylarnino, lower alkylthio, or cycloalkyl; $R_3$ and $R_5$ are each independently H or lower alkyl;

$R_4$ is

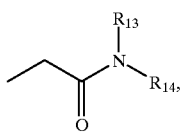

where $R_{13}$ is H, lower alkyl, phenyl or benzyl, and $R_{14}$ is H aryl, aralkyl, or especially

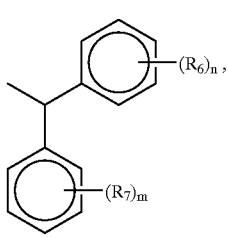

where $R_6$ and $R_7$ are each independently H, OH, $NH_2$, CN, $NO_2$, lower alkyl, halo-lower alkyl, lower alkoxy, lower alkylamino, lower alkylthio, or cycloalkyl, and n and m are each independently an integer from 1 to 3 inclusive; and pharmaceutically acceptable acid addition salts thereof.

The term "alkyl" as used herein refers to saturated hydrocarbon radicals containing from 1 to 30 carbon atoms, inclusive. Alkyl radicals may be straight, branched, or cyclic. Exemplary alkyl radicals include n-pentyl, n-hexyl, n-octyl, n-dodecyl, 2-dodecyl, 4-octadecyl, 3,5-diethylcyclohexyl, duryl, and the like. The term "lower alkyl" as used herein refers to straight, branched, and cyclic chain hydrocarbon radicals having from 1 to 8 carbon atoms, such as methyl, ethyl, propyl, isopropyl, n-butyl, s-butyl, t-butyl, n-pentyl, n-hexyl, cyclopentyl, cyclohexyl, 2-methylcyclopentyl, cyclopentylacetyl, and the like. "Alkoxy" refers to radicals of the formula —OR, where R is alkyl as defined above: "lower alkoxy" refers to alkoxy radicals wherein R is lower alkyl. "Hydroxy-lower alkyl" refers to radicals of the formula HO—R—, where R is lower alkylene of 1 to 8 carbons, and may be straight, branched, or cyclic. "Hydroxy-lower alkoxy" refers to radicals of the formula HO—R—O—, where R is lower alkylene of 1 to 8 carbons, and may be straight, branched, or cyclic. "Lower alkoxy-lower alkyl" refers to groups of the formula $R_aO—R_b—$, where $R_a$ and $R_b$ are each independently lower alkyl. "Lower alkoxy-lower alkoxy" refers to groups of the formula $R_aO—R_bO—$, where $R_a$ and $R_b$ are each independently lower alkyl. "Alkenyl" refers to hydrocarbon radicals of 2–20 carbon atoms having one or more double bonds. Alkenyl radicals may be straight, branched, or cyclic. Exemplary alkenyl radicals include 1-pentenyl, 3-hexenyl, 1,4-octadienyl, 3,5-diethylcyclohexenyl, and the like. "Lower alkenyl" refers to alkenyl radicals having 2–8 carbon atoms.

The term "alkynyl" refers to hydrocarbon radicals of 2–20 carbon atoms having one or more triple bonds. Alkynyl radicals may be straight, branched, or cyclic. Exemplary alkynyl radicals include 1-pentynyl, 3-hexynyl, octa-2-yn-6-enyl, 3,5-diethylcyclohexynyl, and the like. "Lower alkynyl" refers to alkynyl radicals having 2–8 carbon atoms.

The term "haloalkyl" refers to an alkyl radical substituted with one or more halogen atoms. Exemplary haloalkyl radicals include trifluoromethyl, 2,2,2-trifluoroethyl, 3-chlorocyclohexyl, 2-bromo-3-chlorocyclohexyl, 2,3-dibromobutyl, and the like.

"Aryl" refers to aromatic hydrocarbons having up to 14 carbon atoms, preferably phenyl, naphthyl, or benzhydryl. "Aryl-lower alkyl" or "aralkyl" refers to radicals of the form Ar—R—, where Ar is aryl and R is lower alkyl. "Aryloxy" refers to radicals of the from Ar—O—, where Ar is aryl. "Aryloxy-lower alkyl" refers to radicals of the form ArO—R—, where Ar is aryl and R is lower alkyl. "Aryl-cycloalkyl" refers to a condensed ring radical having at least one aromatic ring, and at least one cycloalkyl ring, for example, 1-indanyl, 5-indanyl, 9-fluorenyl, 5,6,7,8-tetrahydronaphthyl, and the like.

The term "acyl" refers to a radical of the formula RCO—, in which R is H, alkyl as defined above, phenyl, benzyl or naphthyl. Exemplary acyl groups include acetyl, propionyl, formyl, t-butoxycarbonyl, benzoyl, and the like. "Lower acyl" refers to radicals wherein R is lower alkyl.

The term "halo" refers to a halogen radical, such as F, Cl, Br, or I.

The term "capping group" refers to a small organic moiety commonly used for protecting amines and amides during synthesis. Exemplary capping groups include, without limitation, methyl, benzhydryl, 4,4'-dimethoxybenzhydryl, and other acylating reagents (e.g., activated acids such as benzoic acids, benzoyl halides or anhydrides), and the like. In general, a capping group will preferably have a molecular weight less than about 500 g/mol, more preferably less than about 300 g/mol, and most preferably less than about 230 g/mol. Presently preferred capping groups include methyl, benzyl, phenyl, phenethyl, benzhydryl, and 4,4'-dimethoxybenzhydryl.

The term "treatment" as used herein refers to reducing or alleviating symptoms in a subject, preventing symptoms from worsening or progressing, inhibition or elimination of the causative agent, or prevention of the infection or disorder in a subject who is free therefrom. Thus, for example, treatment may be reduction of or the prevention of metastasis in a patient having or susceptible to having a metastatic tumor.

The term "uPA- or uPAR-mediated disorder" refers to a disease state or malady which is caused or exacerbated by a biological activity of uPA or uPAR. The primary biological activity exhibited is plasminogen activation. Disorders mediated by plasminogen activation include, without limitation, inappropriate angiogenesis (e.g., diabetic retinopathy, corneal angiogenesis, Kaposi's sarcoma, and the like), metastasis and invasion by tumor cells, and chronic inflammation (e.g., rheumatoid arthritis, emphysema, and the like). Fucosylated ATF is also mitogenic for some tumor cells (e.g., SaOS-2 osteosarcoma cells), which sometimes self-activate in an autocrine mechanism. Accordingly, the huPAR antagonist of the invention is effective in inhibiting the proliferation of uPA-activated tumor cells.

The term "effective amount" refers to an amount of huPAR antagonist compound sufficient to exhibit a detectable therapeutic effect. The therapeutic effect may include, for example, without limitation, inhibiting the growth of undesired tissue or malignant cells, inhibiting inappropriate angiogenesis, limiting tissue damage caused by chronic inflammation, and the like. The precise effective amount for a subject will depend upon the subject's size and health, the nature and severity of the condition to be treated, and the like. Thus, it is not possible to specify an exact effective amount in advance. However, the effective amount for a given situation can be determined by routine experimentation based on the information provided herein.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

General Methods and Detailed Description

Compounds of the invention are easily synthesized by standard chemical methods. The presently-preferred method of synthesis is the "submonomer" technique described by P. Bartlett et aL., WO91/19735, incorporated herein by reference. Briefly, an amine (generally bound to a solid phase) is acylated by a reactant having a carbonyl group and a leaving group (and optionally a side chain) to form an amide. This reaction is conducted under standard conditions for acylation of an amine, as described by Bartlett et al. The acylating reagent is preferably in the form of an "activated" carbonyl, e.g., as an anhydride, acyl halide, carbonate, or the like. The leaving group is then displaced with a primary or secondary amine under conditions appropriate for $S_N2$ displacement, as shown in the Scheme below:

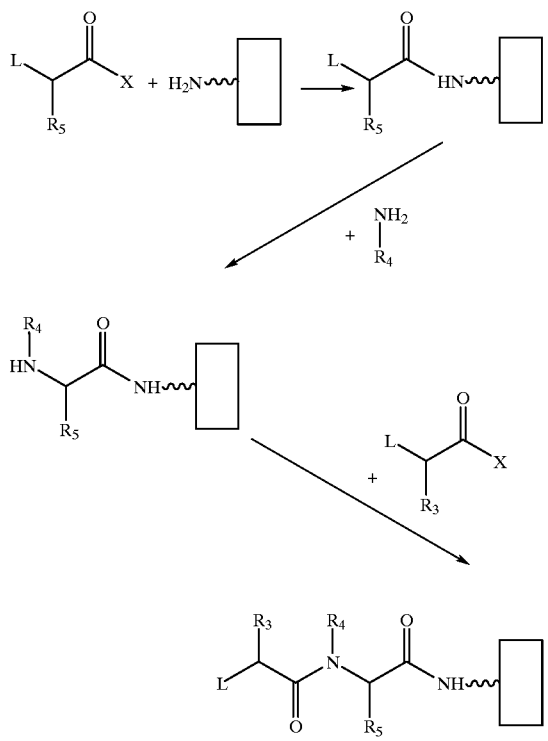

The cycles of acylation and $S_N2$ displacement are repeated until a compound of the desired size is obtained. Either the terminal amine or the terminal amide may be "capped" with a suitable capping group, such as methyl or 4,4'-dimethoxybenzhydryl, for example by reacting the compound with 4,4'-dimethoxybenzhydryl alcohol under acidic conditions following cleavage from the synthesis resin.

The reactants employed in synthesis of the compounds are generally commercially available. Other reactants (e.g., less-common substituted amines) may be prepared by standard chemical means from amines that are commercially available.

Compounds of the invention may be assayed for activity using standard protocols. For example, one may employ the protocol demonstrated in the Examples below to determine binding of compounds of the invention to any desired receptor subtype (e.g., using different sources of tissue). Compounds which exhibit strong binding to receptors will exert either agonistic or (more usually) antagonistic activity, which may be determined by means of appropriate tissue-based or in vivo assays known in the art. Compounds within the scope of the invention may easily be assayed for activity by standard receptor-binding assays.

Compounds of the invention may be screened for activity following any generally suitable assay for urokinase activity or inhibition. A particularly useful assay described in Goodson et al., *Proc Natl Acad Sci USA* (1994) 91:7129 (incorporated herein by reference). One may substitute fragments of urokinase for the intact molecule (e.g., one may use the EGF-like binding domain alone, without the enzymatically-active portion of uPA). In general, the compounds should be tested against uPA receptors derived from the species to be treated, as some species specificity is known to exist.

Compounds of the invention are administered orally, topically, or by parenteral means, including subcutaneous and intramuscular injection, implantation of sustained release depots, intravenous injection, intranasal administration, and the like. When used to treat tumors, it may be advantageous to apply the compound directly to the site, e.g., during surgery to remove the bulk of the tumor. Accordingly, compounds of the invention antagonist may be administered as a pharmaceutical composition comprising the compound in combination with a pharmaceutically acceptable excipient. Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antirnicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Other topical formulations include aerosols, bandages, and other wound dressings. Alternatively, one may incorporate or encapsulate the compound in a suitable polymer matrix or membrane, thus providing a sustained-release delivery device suitable for implantation near the site to be treated locally. Other devices include indwelling catheters and devices such as the Alzet® minipump. Ophthalmic preparations may be formulated using commercially available vehicles such as Sorbicare® (Allergan), Neodecadron® (Merck, Sharp & Dohme), Lacrilube®, and the like, or may employ topical preparations such as that described in U.S. Pat. No. 5,124,155, incorporated herein by reference. Further, one may provide a compound of the invention in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (Mack Pub. Co.).

The amount of compound required to treat any particular disorder will of course vary depending upon the nature and severity of the disorder, the age and condition of the subject, and other factors readily determined by one of ordinary skill in the art. The appropriate dosage may be determined by one of ordinary skill by following the methods set forth below in the examples. As a general guide, about 0.01 mg/Kg to about 50 mg/Kg compound administered i.v. or subcutaneously is effective for inhibiting tissue damage due to chronic inflammation. For treating corneal angiogenesis, the compound may be administered locally in a gel or matrix at a concentration of about 0.001 mg/Kg to about 5 mg/Kg.

EXAMPLES

The examples presented below are provided as a further guide to the practitioner of ordinary skill in the art, and are not to be construed as limiting the invention in any way.

Example 1
(Synthesis of Compounds of the Invention)

A.) Preparation of CHIR 5585

1.) Loading Bromoacetic Acid on Wang Resin

Rink resin (2.71 g, 1.98 mmole) with substitution 0.73 mmole/g is swollen with 15 mL dichloromethane (DCM) in a 50 mL reaction vessel and drained later. Bromoacetic acid (1.12 g, 8 mmole) is mixed with 1M DCC/NMP (8 mL, 8 mmole) and 10 mL DCM. Dimethyl-aminopyridine (58.5 mg, 0.48 mmole) is added into the resin. 18 mL of activated Bromoacetic acid/DCC/NMP/DCM solution is then added into the reaction vessel. The resin mixture is shaken for 60 min at room temperature and then drained and washed with 15 mL DCM 3×, 15 mL DMF 2× and 15 mL IPA. The loaded resin (1) is dried under vacuo to provide bromoacetyl.

2.) Adding N-(4,4'-dimethoxybenzhydryl)glycinamide

Loaded resin (200 mg, 100 μmole)(1) is swollen with 2 mL DMSO in a 8 mL reaction vessel, and then drained. Fmoc-protected N-(4,4'-dimethoxybenzhydryl)-glycinamide (5 mmole) is mixed with DMSO (1.907 mL) to prepare a 2.5 mL solution of 2 M 2-aminoethylamide which is then added to the reaction vessel. The resin mixture is shaken at 45° C. for 4 hr, then drained and washed with 3 mL DMF 6× and 3 mL DCM 6×. to provide the loaded resin (2).

3.) Acylating Resin with Bromoacetic Acid (BAA)

The loaded resin (2) is swollen with 3 mL DCM in a 8 mL reaction vessel and then drained. BAA (84 μl, 750 μmole) is mixed with DIEA (128 μl, 750 μmole) and DCM (2.2 mL) to prepare a 2.5 mL of 0.3 M BAA/DIEA/DCM solution which is then added to the reaction vessel. The resin mixture is shaken for 20 min at room temperature and then drained and washed with 3 mL DCM. The resin sample is treated with 2.5 mL of 0.3 M BAA/DIEA/DCM solution for 20 min again. It is drained and then washed with 3 mL DCM 6× and 3 mL DMF 6× to provide the loaded resin (3).

4.) Coupling Resin with 5-aminoindane

The loaded resin (3) is swollen with 2 mL DMSO in a 8 mL reaction vessel and then drained. 5-Aminoindane (2.5 mmole) was dissolved in DMSO (2.5 mL) to prepare a 2.5 mL of 1 M 5-aminoindane-DMSO solution which is then added to the reaction vessel. The resin mixture is shaken at 45° C. for 4 hr. It is then drained and washed with 3 mL DMF 6× and 3 mL DCM 6× to provide the loaded resin (4).

5.) Acylating Resin with Bromoacetic Acid (BAA)

BAA (84 μl, 750 μmole) is added to resin (4) as described above in part 3.) to provide acylated resin (5). Alternatively, the compound may be capped at this point (as a dimer) by acylation with a carboxylic acid.

6.) Coupling Resin with 4-hydroxyphenethylamine

The loaded resin (5) is swollen with 2 mL DMSO in a 8 mL reaction vessel and then drained. 4-Hydroxyphenethylamine (10 mmole) is dissolved in DMSO (2.5 mL) to prepare a 2.5 mL of 2 M 4-hydroxyphenethylamine/DMSO solution which is then added to the reaction vessel. The resin mixture is shaken at 45° C. for 4 hr. It is then drained and washed with 3 mL DMF 6× and 3 mL DCM 6× to provide the loaded resin (6), which is dried under vacuo.

7.) Cleaving Resin Product

The dried resin (6) is put in a 8 mL reaction vessel. 3 mL of 90% trifluoroacetic acid/water is added into the reaction vessel. The resin is cleaved in TFA for 20 min at room temperature and then filtered into a 50 mL collection tube. All filtrate is concentrated to dryness under vacuo to give (7) (CHIR 5585).

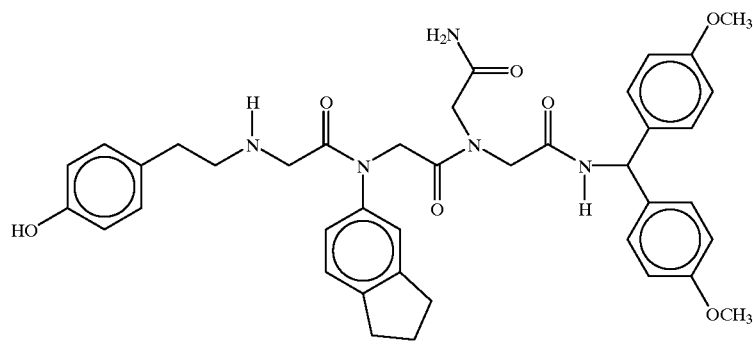

B.) Preparation of additional compounds

1.) CHIR 6696:

Compound CHIR 6696 was prepared following steps 1–4 of Part A above. The loaded resin (4) was treated with phenylacetyl chloride in DCM/pyridine, then cleaved as set forth in step 7 to produce CHIR 6696:

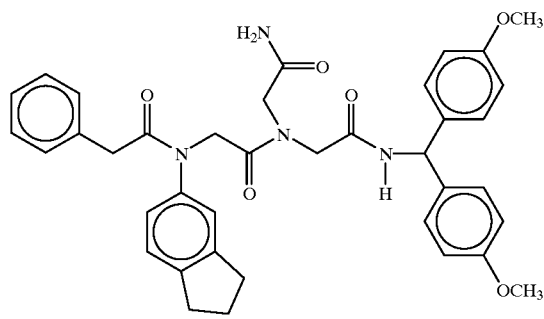

2.) CHIR 10382:

CHIR 10382 was prepared following part A above, but substituting methylamine for N-(4,4'-dimethoxybenzhydryl) glycinamide in step 2. The resulting compound was cleaved from the resin and capped with 4,4'-dimethoxybenzhydryl alcohol in 10% $H_2SO_4$/dioxane to provide CHIR 10382:

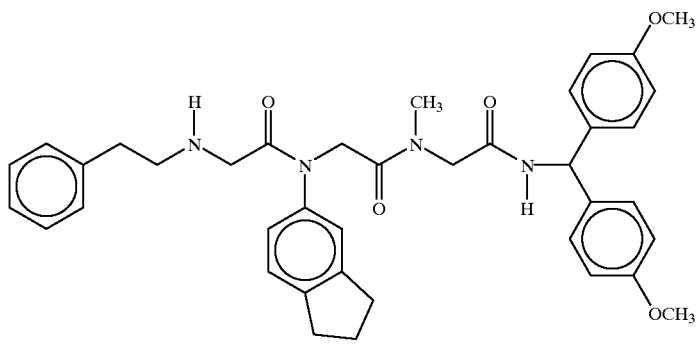

3.) CHIR 6714:
CHIR 6714 was prepared in the same manner as CHIR 10382 above, but substituting ammonia for N-methylglycinamide.

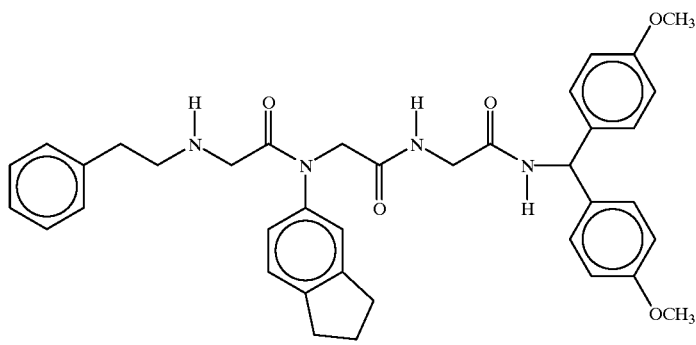

C.) Preparation of Other Compounds
Similarly, proceeding as in part A.) above, the following compounds were made:

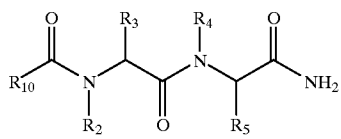

| CHIR # | $R_{10}$ | $R_2$ | $R_3$ | $R_4$ | $R_5$ |
|---|---|---|---|---|---|
| 5585 | 4-hydroxyphenethyl-aminomethyl | 5-indanyl | H | 4,4'-dimethoxybenzhydryl-glycinamide | H |
| 5948 | phenethylaminomethyl | 5-indanyl | H | 4,4'-dimethoxybenzhydryl-glycinamide | H |
| 5949 | 2,4,6-trihydroxyphen-ethylaminomethyl | 5-indanyl | H | 4,4'-dimethoxybenzhydryl-glycinamide | H |
| 5950 | 4-hydroxybutylamino-methyl | 5-indanyl | H | 4,4'-dimethoxybenzhydryl-glycinamide | H |
| 5951 | benzylaminomethyl | 5-indanyl | H | 4,4'-dimethoxybenzhydryl-glycinamide | H |
| 5952 | propynylaminomethyl | 5-indanyl | H | 4,4'-dimethoxybenzhydryl-glycinamide | H |
| 5953 | 4-methoxyphenethyl-aminomethyl | 5-indanyl | H | 4,4'-dimethoxybenzhydryl-glycinamide | H |
| 5954 | 4-hydroxyphenethyl-aminomethyl | phenyl | H | 4,4'-dimethoxybenzhydryl-glycinamide | H |
| 5955 | 4-hydroxyphenethyl-aminomethyl | 4-phenyl-phenyl | H | 4,4'-dimethoxybenzhydryl-glycinamide | H |

-continued

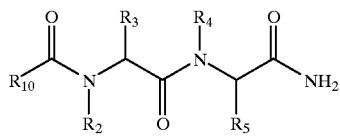

| CHIR # | R₁₀ | R₂ | R₃ | R₄ | R₅ |
|---|---|---|---|---|---|
| 5956 | 4-hydroxyphenethyl-aminomethyl | phenethyl | H | 4,4'-dimethoxybenzhydryl-glycinamide | H |
| 5957 | 4-hydroxyphenethyl-aminomethyl | cyclohexyl | H | 4,4'-dimethoxybenzhydryl-glycinamide | H |
| 5958 | 4-hydroxyphenethyl-aminomethyl | 3-methyl-enedioxy-phenyl | H | 4,4'-dimethoxybenzhydryl-glycinamide | H |
| 5959 | 4-hydroxyphenethyl-aminomethyl | 5-indanyl | H | 9-fluorenylglycinamide | H |
| 5960 | 4-hydroxyphenethyl-aminomethyl | 5-indanyl | H | 4-methoxybenzylglycinamide | H |
| 5961 | 4-hydroxyphenethyl-aminomethyl | 5-indanyl | H | benzhydrylglycinamide | H |
| 5991 | 4-hydroxyphenethyl-aminomethyl | 5-indanyl | Me | 4,4'-dimethoxybenzhydryl-glycinamide | H |
| 5992 | 4-hydroxyphenethyl-aminomethyl | 5-indanyl | Me | 4,4'-dimethoxybenzhydryl-glycinamide | H |
| 5990 | 1-(4-hydroxyphen-ethylamino)ethyl | 5-indanyl | H | 4,4'-dimethoxybenzhydryl-glycinamide | H |
| 5993 | 1-(4-hydroxyphen-ethylamino)ethyl | 5-indanyl | H | 4,4'-dimethoxybenzhydryl-glycinamide | Me |
| 5994 | 4-hydroxyphenethyl-aminomethyl | 5-indanyl | Me | 4,4'-dimethoxybenzhydryl-glycinamide | Me |
| 5995 | 1-(4-hydroxyphen-ethylamino)ethyl | 5-indanyl | H | 4,4'-dimethoxybenzhydryl-glycinamide | H |
| 6696 | benzyl | 5-indanyl | H | 4,4'-dimethoxybenzhydryl-glycinamide | H |
| 6697 | phenethyl | 5-indanyl | H | 4,4'-dimethoxybenzhydryl-glycinamide | H |
| 6698 | phenyl | 5-indanyl | H | 4,4'-dimethoxybenzhydryl-glycinamide | H |
| 11509 | propynylaminomethyl | 2-naphthyl | H | 4,4'-dimethoxybenzhydryl-glycinamide | H |
| 11648 | 4-hydroxyphenethyl-aminomethyl | 2-naphthyl | H | 4,4'-dimethoxybenzhydryl-glycinamide | H |
| 11649 | 4-aminophenethyl-aminomethyl | 2-naphthyl | H | 4,4'-dimethoxybenzhydryl-glycinamide | H |
| 11650 | 2-furylmethylamino-methyl | 2-naphthyl | H | 4,4'-dimethoxybenzhydryl-glycinamide | H |
| 11652 | propynylaminomethyl | 3,4-di-methyl-phenyl | H | 4,4'-dimethoxybenzhydryl-glycinamide | H |
| 11653 | benzylaminomethyl | 2-naphthyl | H | 4,4'-dimethoxybenzhydryl-glycinamide. | H |

Example 2

(Assay for uPA inhibitory Activity)

Compounds prepared as described in Example 1 above were screened in a human urokinase receptor radio ligand competition assay, as described in Goodson et al., *Proc Natl Acad Sci USA* (1994) 91:7129 (incorporated herein by reference), except that the labeled ligand used was an epitope tagged version of the EGF-like domain of human urokinase, expressed and purified from recombinant yeast. The activities observed are set forth in the Table below:

| CHIR# | IC$_{50}$ (µM) | % Inhibition | Concentration (µM) |
|---|---|---|---|
| 11509 | 0.033 | | |
| 11648 | | 80 | 1 |
| 11649 | | 80 | 1 |
| 11650 | | 80 | 1 |
| 11651 | | 40 | 1 |
| 11652 | | 30 | 1 |
| 11653 | | 85 | 1 |
| 10382 | 0.5 | | |
| 6714 | 10.0 | | |
| 5440 | | 22.5 | 10 |
| 5585 | 0.2 | | |
| 5948 | 1.38 | | |
| 5949 | 2.6 | | |
| 5950 | 0.76 | 51.4 | 1 |
| 5951 | 0.77 | 43.5 | 0.2 |
| 5952 | 0.7 | 32.8 | 0.2 |
| 5953 | 0.44 | 72.5 | 1 |
| 5954 | 1.8 | | |
| 5955 | 1.9 | 36.6 | 0.2 |
| 5956 | ~10 | 24.1 | 2.5 |
| 5957 | >10 | 19.3 | 0.2 |

-continued

| CHIR# | IC$_{50}$ ($\mu$M) | % Inhibition | Concentration ($\mu$M) |
|---|---|---|---|
| 5958 | 3.7 | 32.3 | 0.2 |
| 5959 |  | 48.7 | 10 |
| 5960 |  | 27.2 | 0.2 |
| 5961 | 0.93 |  |  |
| 5990 | 0.105 |  |  |
| 5991 |  | 31.8 | 0.2 |
| 5992 |  | 10.9 | 0.1 |
| 5993 | 0.12 | 27.2 | 0.1 |
| 5994 |  | 4.2 | 0.1 |
| 5995 |  | 20.5 | 0.1 |
| 6696 | 1.65 | 43.2 | 1.0 |
| 6697 | 0.2 | 80 | 1.0 |
| 6698 |  | 63.6 | 10 |

What is claimed:

1. A compound of the formula:

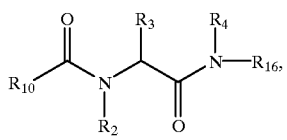

where $R_{10}$ is

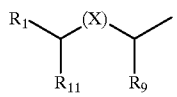

or a capping group, where X is $NR_{12}$, $CR_{12}R_{15}$, O, S, $SR_{12}$, or $SR_{12}R_{15}$; $R_1$, $R_9$, $R_{11}$, $R_{12}$, $R_{15}$ are each independently H, lower alkyl, lower alkenyl, lower alkynyl, aryl, aralkyl, aryl-alkenyl, aryl-alkynyl, aryl-cycloalkyl, unsubstituted or substituted with 1–3 halo, OH, $NH_2$, lower alkyl, halo-lower alkyl, lower alkoxy, lower alkylarino, lower alkylthio, CN or $NO_2$;

$R_{16}$ is

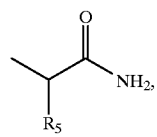

H, lower alkyl, cycloalkyl, or lower alkenyl; $R_2$ is aryl or aralkyl, unsubstituted or substituted with 1–3 halo, OH, $NH_2$, CN, $NO_2$, lower alkyl, halo-lower alkyl, lower alkoxy, lower alkylamino, lower alkylthio, or cycloalkyl;

$R_3$ and $R_5$ are each independently H or lower alkyl;

$R_4$ is

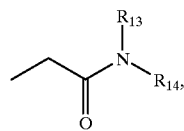

where $R_{13}$ is H, lower alkyl, phenyl or benzyl, and $R_{14}$ is H, aryl, aralkyl, or

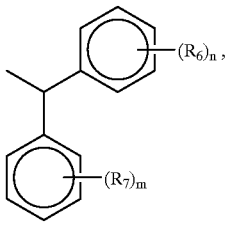

where $R_6$ and $R_7$ are each independently H, OH, $NH_2$, CN, $NO_2$, lower alkyl, halo-lower alkyl, lower alkoxy, lower alkylamino, lower alkylthio, or cycloalkyl, and n and m are each independently an integer from 1 to 3 inclusive;

and pharmaceutically acceptable acid addition salts thereof.

2. The compound of claim 1, wherein $R_4$ is

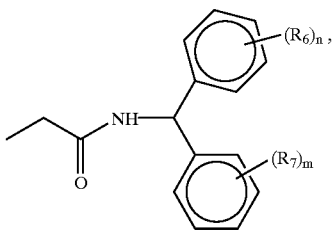

and n and m are each 1, and $R_6$ and $R_7$ are each 4-methoxy, and $R_{16}$ is

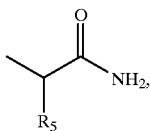

where $R_5$ is H.

3. The compound of claim 2, wherein $R_2$ is selected from the group consisting of 2-naphthyl and 5-indanyl.

4. The compound of claim 3, wherein $R_{10}$ is

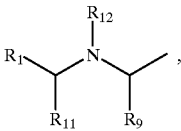

where $R_9$, $R_{11}$, and $R_{12}$ are each H, and

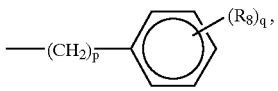

R₁ is selected from the group consisting of

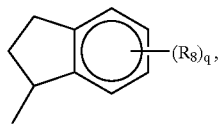

and —C≡CH, where p is an integer from 0 to 6, q is an integer from 0 to 3, and R₈ is OH, NH₂, CN, NO₂, lower alkyl, halo-lower alkyl, lower alkoxy, lower alkylamino, lower alkylthio, or cycloalkyl.

5. The compound of claim 4, wherein R₃ is H.

6. The compound of claim 5, wherein R₁ is —C≡CH, and R₂ is 2-naphthyl.

7. The compound of claim 5, wherein R₁ is

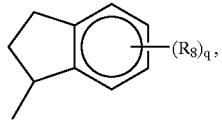

q is 0, and R₂ is 2-naphthyl.

8. The compound of claim 5, wherein R₁ is

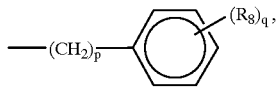

where p is 1, q is 1, R₂ is 2-naphthyl, and R₈ is OH.

9. The compound of claim 5, wherein R₁ is

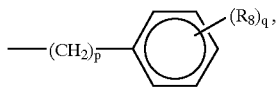

where p is 1, q is 1, R₂ is 2-naphthyl, and R₈ is NH₂.

10. The compound of claim 5, wherein R₁ is

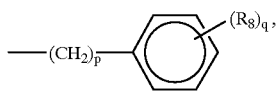

where p is 0, q is 0, and R₂ is 2-naphthyl.

11. The compound of claim 5, wherein R₁ is

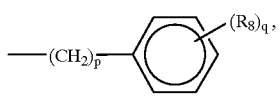

where p is 1, q is 1, R₂ is 5-indanyl, and R₈ is OH.

12. The compound of claim 1, wherein R₄ is

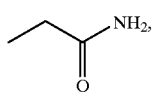

R₃ and R₅ are each H, R₁ is

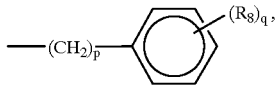

where p is 1, q is 1, R₂ is 5-indanyl, and R₈ is OH.

13. The compound of claim 1, wherein R₄ is

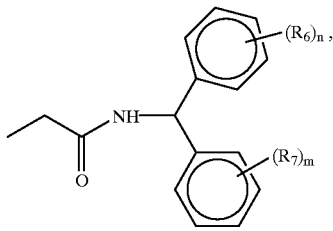

and n and m are each 1, and R₆ and R₇ are each 4-methoxy, and

R₁₆ is H or lower alkyl.

14. The compound of claim 13, wherein R₁₀ is benzyl, phenyl, phenethyl, 4-hydroxybenzyl, or 4-hydroxyphenethyl.

15. The compound of claim 14, wherein R₃ is H, and R₂ is 5-indanyl.

16. The compound of claim 15, wherein R₁₀ is phenethyl.

17. The compound of claim 16, wherein R₁₆ is methyl.

18. A composition comprising:
a compound of the formula

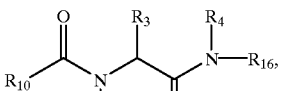

where
R₁₀ is

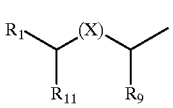

or a capping group, where X is NR₁₂, CR₁₂R₁₅, O, S, SR₁₂, or SR₁₂R₁₅; R₁, R₉, R₁₁, R₁₂ R₁₅ are each independently H, lower alkyl, lower alkenyl, lower alkynyl, aryl, aralkyl, aryl-alkenyl, aryl-alkynyl, aryl-cycloalkyl, unsubstituted or substituted with 1–3 halo, OH, NH₂, lower alkyl, halo-lower alkyl, lower alkoxy, lower alkylamino, lower alkylthio, CN or NO₂;

R₁₆ is

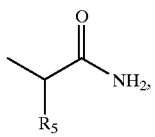

H, lower alkyl, cycloalkyl, or lower alkenyl;

R₂ is aryl or aralkyl, unsubstituted or substituted with 1–3 halo, OH, NH₂, CN, NO₂, lower alkyl, halo-lower alkyl, lower alkoxy, lower alkylamino, lower alkylthio, or cycloalkyl;

R₃ and R₅ are each independently H or lower alkyl;

R₄ is

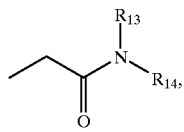

where R₁₃ is H, lower alkyl, phenyl or benzyl, and R₁₄ is H, aryl, aralkyl, or

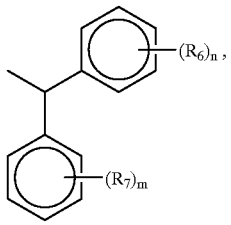

where R₆ and R₇ are each independently H, OH, NH₂, CN, NO₂, lower alkyl, halo-lower alkyl, lower alkoxy, lower alkylamino, lower alkylthio, or cycloalkyl, and n and m are each independently an integer from 1 to 3 inclusive;

or a pharmaceutically acceptable salt thereof; and a pharmaceutically acceptable excipient.

* * * * *